United States Patent
Buesing et al.

(10) Patent No.: US 6,740,767 B1
(45) Date of Patent: May 25, 2004

(54) METHOD OF MAKING SULFUR CONTAINING ORGANOSILICON COMPOUNDS

(75) Inventors: Chad Aaron Buesing, Midland, MI (US); John Michael Gohndrone, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 14 days.

(21) Appl. No.: 10/293,841

(22) Filed: Nov. 12, 2002

(51) Int. Cl.$^7$ ................................................. C07F 7/08
(52) U.S. Cl. ...................................................... 556/427
(58) Field of Search ......................................... 556/427

(56) References Cited

U.S. PATENT DOCUMENTS

| | | | |
|---|---|---|---|
| 5,405,985 A | 4/1995 | Parker et al. | 556/427 |
| 5,468,893 A | 11/1995 | Parker et al. | 556/427 |
| 5,583,245 A | 12/1996 | Parker et al. | 556/427 |
| 5,663,396 A | 9/1997 | Musleve et al. | 556/427 |
| 6,534,668 B2 * | 3/2003 | Backer et al. | 556/427 |

* cited by examiner

Primary Examiner—Samuel Barts
(74) Attorney, Agent, or Firm—Jin L. DeCesare

(57) ABSTRACT

A process for producing organosilicon compounds of the formula $(RO)_{3-m}R_mSi—Alk—S_n—Alk—SiR_m(OR)_{3-m}$ in which R is a monovalent hydrocarbon having 1–12 carbon atoms, Alk is a divalent hydrocarbon having 1–18 carbon atoms, m is 0, 1 or 2, and n is 2–8, preferably 3–8. The process consists generally of the steps of (I) heating and reacting (A) a sulfide compound such as $M_2S_n$ or MHS where H is hydrogen, M is ammonium or an alkali metal, and n is 1–8; with (B) a silane compound of the formula $(RO)_{3-m}R_mSi—Alk—X$ where X is Cl, Br or I, and m is 0, 1, or 2; and with (C) sulfur. Step (I) is carried out in the presence of a phase transfer catalyst, and an aqueous phase containing a buffer or a basic compound, to form a product mixture. In step (II), the product mixture is again heated to a temperature of 80–100° C., preferably a temperature of 85–95° C., and most preferably to a temperature of 87–92° C., for about 1–3 hours, and the desired organosilicon compound can be obtained by separating it from the resulting product mixture. The result is a composition with improved color.

8 Claims, No Drawings

METHOD OF MAKING SULFUR CONTAINING ORGANOSILICON COMPOUNDS

FIELD OF THE INVENTION

This invention is related to an improved method of making sulfur containing organosilicon compounds possessing better color. In particular, products with lighter colors can be obtained by modifying certain existing processes.

BACKGROUND OF THE INVENTION

Sulfur containing organosilicon compounds are known to be useful as reactive coupling agents in a variety of commercial applications. In particular, sulfur containing organosilicon compounds have become a necessary component in the production of tires based on rubber vulcanates containing silica. In that application, the sulfur containing organosilicon compounds improve the physical properties of rubber vulcanates containing silica, resulting in automotive tires with improved abrasion resistance, rolling resistance, and wet skidding performance. The sulfur containing organosilicon compounds can be added directly to the silica containing rubber vulcanates, or they can be used to pre-treat silica prior to addition to the rubber vulcanate compositions.

While a number of processes are known in the art for making such sulfur containing organosilicon compounds, a preferred one of such processes is described in a copending U.S. patent application Ser. No. 09/895,719, filed Jun. 29, 2001, entitled "Preparation of Sulfur Containing Organosilicon Compounds Using a Buffered Phase Transfer Catalysis Process". The copending application is assigned to the same assignee as the present invention.

The process according to the copending application involves reacting (A) a sulfide compound having the formula $M_2S_n$ or MHS where H is hydrogen, M is ammonium or an alkali metal, and n is 1–8, with (B) a silane compound with the formula $(RO)_{3-m}R_mSi$—Alk—X where X is Cl, Br or I, and m is 0, 1, or 2, and (C) sulfur. The reaction is carried out in the presence of a phase transfer catalyst and an aqueous phase containing a buffer. This process is characterized by addition of buffers to the aqueous phase which minimizes and/or prevents gelling of the sulfur containing organosilicon compounds.

The process according to the present invention, while being similar to the process described in the copending application, is not the same and is a significant improvement thereof. According to the present invention, it was discovered that one can dramatically reduce the color and any residual catalyst species present in the organic phase by heating the two phase product mixture in an additional step to a temperature of 80–100° C., preferably a temperature of 85–95° C., and most preferably a temperature of 87–92° C. The heating should be continued for about 1–3 hours. This additional heating step results in a mild oxidation process which is enhanced by the basic species remaining in the aqueous phase, after completion of the reaction step in the process according to the copending application. This improvement is especially significant for commercial products where n corresponds to values of 3 or 4, or more, as product color is an important quality issue. Thus, there is a perception in the market place that quality is associated with less color. By implementing this additional heating step, one is enabled to obtain significant reductions of color of sulfur containing organosilicon compounds.

SUMMARY OF THE INVENTION

This invention is directed to a process for producing organosilicon compounds having the formula $(RO)_{3-m}R_mSi$—Alk—$S_n$—Alk—$SiR_m(OR)_{3-m}$. In the formula, R represents independently a monovalent hydrocarbon having 1–12 carbon atoms, Alk represents a divalent hydrocarbon having 1–18 carbon atoms, m is an integer representing 0,1 or 2, and n is an integer with a value of 2–8, preferably 3–8, representing the average sulfur-chain length, i.e., the sulfur rank. The process consists generally of the steps of (I) heating and reacting (A) a sulfide compound having the formula $M_2S_n$ or MHS wherein H is hydrogen, M is ammonium or an alkali metal, and n is 1–8, with (B) a silane compound having the formula $(RO)_{3-m}R_mSi$—Alk—X wherein X is Cl, Br or I; R and Alk are the same as defined above; and m is 0, 1, or 2, and (C) sulfur, in the presence of a phase transfer catalyst and an aqueous phase containing a buffer or a basic compound, to form a product mixture.

In a step (II), the product mixture, unlike the product mixtures manufactured according to previously known processes, is again heated but to a temperature of 80–100° C., preferably a temperature of 85–95° C., and most preferably to a temperature of 87–92° C., and then the desired organosilicon compound is obtained by separating it from the heated product mixture in a third step (III).

Separations can be obtained, for example, by (D) adding water or a dilute acidic solution to the product mixture, and (E) phase separating the product mixture into an organic phase containing the organosilicon compound and an aqueous phase. The organic phase containing the organosilicon compound can then be dried by (i) heating the organic phase at a reduced pressure, or (ii) drying it by contacting it with a solid desiccant such as sodium sulfate, magnesium sulfate, calcium sulfate, calcium chloride, magnesium chloride, lithium chloride, a molecular sieve, zeolite, aluminasilicate, or silica gel. The preferred desiccants are sodium sulfate and magnesium sulfate.

Other processing techniques can be included as steps according to the present invention such as the additional steps of (F) cooling the organic phase containing the organosilicon compound to a temperature below 15° C. to precipitate unreacted sulfur compounds, and (G) separating the organic phase containing the organosilicon compound from the precipitated unreacted sulfur compounds.

These and other features of the invention will become apparent from a consideration of the detailed description.

DETAILED DESCRIPTION OF THE INVENTION

As noted above, the process herein involves the preparation of sulfur containing organosilicon compounds of the general formula $(RO)_{3-m}R_mSi$—Alk—$S_n$—Alk—$SiR_m(OR)_{3-m}$ in which R is a monovalent hydrocarbon having 1–12 carbon atoms, Alk is a divalent hydrocarbon having 1–18 carbon atoms, m is 0, 1 or 2, and n is 2–8, preferably 3–8. It consists generally of the steps of (I) heating and reacting (A) a sulfide compound such as $M_2S_n$ or MHS where H is hydrogen, M is ammonium or an alkali metal, and n is 1–8; with (B) a silane compound of the formula $(RO)_{3-m}R_mSi$—Alk—X where X is Cl, Br or I; R and Alk are the same as defined above; and m is 0, 1, or 2; and with (C) sulfur. Step (I) is carried out in the presence of a phase transfer catalyst, and an aqueous phase containing a buffer or a basic compound, to form a product mixture. In step (II), the product mixture is again heated but to a temperature of 80–100° C., preferably a temperature of 85–95° C., and most preferably to a temperature of 87–92° C., for a period of time of about 1–3 hours, and the desired organosilicon compound can be obtained by separating it from the resulting product mixture.

Some examples of sulfur containing organosilicon compounds which nay be prepared according to the present invention are described generally in U.S. Pat. No. 5,405,985 (Apr. 11, 1995); U.S. Pat. No. 5,468,893 (Nov. 21, 1995); U.S. Pat. No. 5,583,245 (Dec. 10, 1996); and U.S. Pat. No. 5,663,396 (Sep. 2, 1997). Preferred sulfur containing organosilicon compounds which can be prepared according to this invention include the 3,3'-bis(trialkoxysilylpropyl) polysulfides such as 3,3'-bis(triethoxysilylpropyl) disulfide and 3,3'-bis(triethoxysilylpropyl) tetrasulfide.

The latter composition, i.e., bis[3-(triethoxysilyl)propyl] tetrasulfide (TESPT) with the formula $[(CH_2H_5O)_3SiCH_2CH_2CH_2—S—S—]_2—$, is shown in more detail below. TESPT is a relatively commercially successful product, and therefore any process which can improve its quality can have significant value in the market place.

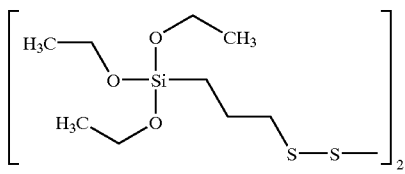

Bis[3-(triethoxysilyl)propyl]tetrasulfide

Sulfide compounds of the formula $M_2S_n$ or MHS are used as component (A) in reaction step (I) of the process, in which M represents an alkali metal or ammonium group, and H represents hydrogen. Some representative alkali metals include lithium, potassium, sodium, rubidium, or cesium, but preferably M is sodium. Some examples of MHS compounds include NaHS, KHS, and NH$_4$HS, and NaHS is preferred. Some examples of particular NaHS compound forms include NaHS flakes containing 71.5–74.5 percent NaHS, and NaHS liquors containing 45–60 percent NaHS, both forms being commercially available from PPG Industries, Inc., Pittsburgh, Pa. $M_2S_n$ compounds of the type $M_2S_n$ include $Na_2S$, $K_2S$, $Cs_2S$, $(NH_4)_2S$, $Na_2S_2$, $Na_2S_3$, $Na_2S_4$, $Na_2S_6$, $K_2S_2$ $K_2S_3$, $K_2S_4$, $K_2S_6$, and $(NH_4)_2S_2$. Preferably, the sulfide compound is $Na_2S$. A preferred form of sulfide compound of this type is sodium sulfide flakes containing 60–63 percent $Na_2S$ which is also available from PPG Industries, Inc., Pittsburgh, Pa.

Component (B) of the process is a silane compound of the formula $(RO)_{3-m}R_mSi$—Alk—X in which R is independently any hydrocarbon group containing 1–12 carbon atoms such as methyl, ethyl, propyl, butyl, isobutyl, cyclohexyl, or phenyl. Preferably, R is methyl or ethyl. In the formula, m is 0, 1 or 2, preferably zero. Alk represents a divalent hydrocarbon group containing 1–18 carbon atoms such as ethylene, propylene, butylene, or isobutylene. Preferably the divalent hydrocarbon group contains 2–4 carbon atoms. Most preferred is a propylene group. X represents a halogen atom such as chlorine, bromine, or iodine, preferably chlorine. Some suitable examples of silane compounds that may be used as component (B) according to the process of the invention include chloropropyltriethoxysilane, chloropropyltrimethoxysilane, chloroethyltriethoxysilane, chlorobutyltriethoxysilane, chloroisobutylmethyldiethoxy silane, chloroisobutylmethyldimethoxysilane, chloropropyldimethylethoxysilane. Preferably, the silane component (B) is chloropropyltriethoxysilane (CPTES).

Sulfur is used as component (C) and can comprise elemental sulfur, such as a 100 mesh refined sulfur powder commercially available from the Sigma-Aldrich Company, Milwaukee, Wis. While the he amount of sulfur (C) and sulfide compound (A) can vary, the molar ratio of $S/M_2S_n$ or the molar ratio of S/MHS should he maintained in the range of from 0.3–5. The molar ratio of sulfur/sulfide compound can be utilized to affect the final product distribution, i.e., the average value of n in the product formula $(RO)_{3-m}R_mSi$—Alk—$S_n$—Alk—$SiR_m(OR)_{3-m}$. For example, when an average value of n of 4 is desired, the range of ratio of sulfur/sulfide compound should be from 2.7–3.2.

The silane compound (B) can be reacted with the sulfide compound (A) in the presence or absence of a solvent, or alternatively, with the sulfide compound (A) and sulfur (C) in combination. The silane compound (B) can also be dispersed in an organic solvent to form an organic phase. Some representative examples of organic solvents include toluene, xylene, benzene, heptane, octane, nonane, decane, and chlorobenzene, preferably toluene. Most preferably, the silane compound (B) is reacted directly with the sulfide compound (A) and sulfur (C) in combination. The amount of the silane compound (B) can also vary, but preferably it is used so as to provide a molar range of 1:10 to 10:1, based on the amount of sulfide compound (A). Thus, when an average value of 4 for n is desired, silane compound (B) is present in an amount corresponding to a 2.0–2.10 molar excess of the $M_2S_n$ sulfide compound (A), with a range of about 2.01–2.06 being most preferred.

Phase transfer catalysts suitable for use according to the invention are quaternary onium cations. Some representative examples of quaternary onium salts yielding quaternary ammonium cations that can be used as phase transfer catalysts are described in U.S. Pat. No. 5,405,985 (Apr. 11, 1995) which was noted above, among which are tetrabutylammonium bromide (TBAB), tetrabutylammonium chloride (TBAC), tetrabutylphosphonium bromide, tetrabutylphosphonium chloride, tetraphenylarsonium bromide, and tetraphenylarsonium chloride. The preferred quaternary onium salts according to this invention are TBAB and TBAC, most preferably TBAB. These materials are available commercially from chemical suppliers such as Sigma-Aldrich, Milwaukee, Wis. The amount of phase transfer catalyst used in the process may vary, but is preferably used in an amount of from 0.1–10 weight percent based on the amount of silane compound (B), most preferably 0.5–2 weight percent. While the catalyst can be added to the reaction at any time, it is preferred to add the catalyst to the aqueous phase prior to the reaction step.

The reaction in step (I) of the process of the invention includes an aqueous phase containing a basic compound such as sodium hydroxide or a buffer. The buffer can consist of a single compound such as alkali metal salts of phosphates, hydrogen phosphates, dihydrogen phosphates, carbonates, hydrogen carbonates, borates, or combinations thereof. Some examples of suitable buffers include $Na_3PO_4$, $Na_2HPO_4$, $NaH_2PO_4$, $Na_2CO_3$, $NaHCO_3$, and $NaBaB_4O_7$. Preferably, the buffer consists of $Na_3PO_4$, $Na_2CO_3$, or $K_2CO_3$. While the amount of basic compound or buffer in the aqueous phase can vary, it is generally added in a molar amount equal to or greater than the number of moles of the sulfide compound (A), i.e., $M_2S_n$ or MHS. The pH of the aqueous phase is controlled by adding the buffer or basic compound at such a rate and concentration so as to maintain a pH during the reaction in the range of 7–14, preferably by using sodium hydroxide.

In one embodiment of the invention, the sulfide compound (A), the phase transfer catalyst, the buffer, water, and sulfur (C) can be mixed together to form an intermediate reaction product. This reaction may be conducted at a variety of temperatures, but generally the temperature is in the range of 40–100° C. Preferably, the reaction is conducted at a temperature ranging from 65–95° C. While step (I) can be conducted at various pressures, it is preferably conducted at atmospheric pressure. The time needed for the reaction of step (I) to occur is not critical, but generally it will range from 5–30 minutes. The intermediate reaction product is then reacted with silane compound (B). The time for reacting the intermediate reaction product and silane compound (B) is not critical, but generally it will range from 5 minutes to 6 hours.

The amount of water used for the aqueous phase can vary, but the amount should be determined based on the amount of silane compound (B) used in the process. The water can be added directly or indirectly, as water may be present in some of the starting materials. For purposes of this invention, the total amount of water includes both water added directly or water added indirectly. In any event, the total amount of water in the aqueous phase or present in the intermediate reaction product should be 1–100 weight percent of the silane compound (B), with a range of 2.5–70 weight percent being preferred. Most preferred is a range of 20–40 weight percent.

The silane compound (B) can be added to the aqueous phase or to the intermediate reaction product at a rate so as to control the exothermic reaction and maintain a temperature in the range of 40–110° C. Preferably the reaction temperature is maintained at a temperature of 60–95° C. Progression of the reaction towards completion can be monitored by the consumption of silane compound (B). The amount of the catalyst and reaction temperature may affect the reaction time necessary for completion however.

At the end of the reaction, a product mixture is produced containing an organic phase, an aqueous phase, and some precipitated solid materials including various salts such as NaCl, $Na_2HPO_4$, and $NaHCO_3$, or their analogous potassium salts, formed during the reaction. The organic phase consists of the desired sulfur containing organosilicon compound.

The improvement in the process according to this invention occurs at this point in the process, in which it was found that one skilled in the art can dramatically reduce the color and any residual catalyst species present in the organic phase by heating the product mixture in a step (II) to a temperature of 80–100° C., preferably a temperature of 85–95° C., and most preferably to a temperature of 87–92° C. and holding for a period of time, preferably 1–3 hours. This additional heating step (II) results in a mild oxidation process which is enhanced by the basic species remaining in the aqueous phase after completion of the reaction step (I), i.e., residual buffer or basic compound such as NaOH. For commercial products where the average n corresponds to values of 2–4, or more, product color is an important quality issue as there is a perception in the market place by consumers of quality being associated with less color. By implementing this oxidation step (II) one is able to obtain a significant reduction of color of sulfur containing organosilicon compounds.

Following step (II), the process includes other steps to enhance separat ion of the sulfur containing organosilicon compound from the oxidized product mixture. This separation can consist of a simple phase separation of organic and aqueous phases. Alternatively, if some precipitated salts have been formed during the reaction, the salts can be separated first by a filtering process or by a decanting method prior to the phase separation. Preferably, additional water or a dilute acidic solution is added to the product mixture prior to separation of the phases. Addition of water or dilute acidic solution can enhance phase separation by dissolving some or all of any existing precipitated salts.

The amount of additional water or dilute acidic solution may vary from 10–50 weight percent, based on the weight of the amount of silane compound (B) used, but preferably it is from 20–40 weight percent, most preferably from 25–35 weight percent. If a dilute acidic solution is employed, one can use any common acid such as HCl, $HNO_3$, or $H_2SO_4$ having a normal (N) concentration of 0.000001–5, preferably 0.01–1. Dilute acidic solutions can be prepared by the addition of a chlorosilane to water. Thus, some examples of chlorosilanes that can be used to create such dilute acidic solution include trichlorosilane, trichloromethylsilane, dimethyldichlorosilane, dimethylchlorosilane, and trimethylchlorosilane. Generally, 0.5–10 weight percent of a chlorosilane is used to prepare the dilute acidic solution, and 1–5 weight percent is the most preferred. Trimethylchlorosilane is a convenient chlorosilane to use for creating such dilute acidic solutions.

Following addition of water or dilute acidic solution to the product mixture, the organosilicon compound is isolated from the product mixture by phase separating the organic phase and aqueous phase. The organic phase consisting of the desired sulfur containing organosilicon compound can be subjected to a drying step. One mode of drying can be to treat the organic phase under a vacuum to remove any volatile organic materials present, along with any residual water. Such drying can be obtained by heating the organic phase to a temperature of 20–160° C. under a reduced pressure of 5–35 mm Hg (0.67–4.65 kPa), preferably 90–120° C. at 5–25 mm Hg (0.67–3.33 kPa). Another way of drying the organic phase can be obtained by means of a thin film stripper for removing volatile organic materials and residual water.

Yet another technique for drying the organic phase is to contact the organic phase consisting of the desired sulfur containing organosilicon compound with a desiccant. The desiccant can comprise any solid material known in the art to remove trace quantities of water present in an organic phase. Some suitable desiccants include hygroscopic materials such as sodium sulfate, magnesium sulfate, calcium sulfate, calcium chloride, magnesium chloride; other metallic halides such as lithium chloride; silicate based materials such as molecular sieves, zeolites, aluminasilicates; and silica gels. The preferred desiccant is sodium sulfate or magnesium sulfate, with sodium sulfate being the most preferred.

If desired, the dried organic phase can be subjected to some additional steps for improving its final purity and appearance. Thus, the organic phase comprising the desired sulfur containing organosilicon compound can be cooled to a temperature below 15° C. This cooling step results in precipitation of any unreacted sulfur and sulfur compound. Preferably, the organic phase is cooled to a temperature in the range of −20 to 30° C., preferably −15 to 15° C. Any precipitated and unreacted sulfur or sulfur compound can be removed by filtration from the organic phase. Removal of unreacted sulfur and sulfur compounds minimizes or eliminates any further precipitation of the sulfur or any unreacted sulfur compounds over time. This results in long term storage stability of the desired sulfur containing organosilicon compound, and enhances its value as the composition will not change over time or result in a product containing undesirable solid precipitates.

EXAMPLES

The following examples are set forth to illustrate the invention in more detail. In these examples, the distribution of the various sulfur containing organosilicon, compounds was analyzed by high performance liquid chromatography (HPLC). The HPLC analysis was conducted generally using about 8–9 drops of the reaction sample which was then diluted in 8.5 g of cyclohexane. The sample was filtered into a vial through a 0.2 $\mu$m polytetrafluoroethylene (PTFE) membrane, available commercially under the tradename Puradisc 25TF from Whatman Inc., Ann Arbor, Mich. A 10 $\mu$l sample of the filtrate was injected via an autosampler into an HPLC system Model 1050 of the Hewlett-Packard Company, Palo Alto, Calif. The sample was fractionated on a Lichrosorp RP18 column marketed by Alltech Associates Inc., Deerfield, Ill. The column was 250 mm×4.6 mm, 10 $\mu$m in size, and the fractionation was carried out using a mixture of 96 percent acetonitrile and 4 percent tetrahydrofuran (vol/vol basis) as the mobile phase.

Fractions were investigated via a UV-absorption detector using 254 nm as the appropriate excitation wavelength. Different UV-sensitivities of single sulfide species were averaged by division of the respective peak area through specific and empirically evaluated response factors (RF). These response factors (RF) are shown below in Table 1. The factors consist of data reported by H. D. Luginsland, in an article entitled *Reactivity of the Sulfur Functions of the Disulfane Silane TESPD and the Tetrasulfane Silane TESPT*, Rubber Division, American Chemical Society, Chicago, Ill., on Apr. 13–16, 1999. This RF data reflects the hyperchromy of each sulfur atom in the chain and elemental sulfur.

TABLE 1

High Performance Liquid Chromatography Response Factors

| S2 | S3 | S4 | S5 | S6 | S7 | S8 | S9 | S10 | $S_{elem.}$ |
|---|---|---|---|---|---|---|---|---|---|
| 1.0 | 3.52 | 6.39 | 9.78 | 13.04 | 17.39 | 20.87 | 26.08 | 31.30 | 37.26 |

Example 1

A 1.5 L jacketed glass reactor equipped with a motor-driven impeller, a single baffle, thermocouple, and an addition funnel, and starting at ambient temperature, was loaded with 55.31 g of water, 114.14 g aqueous NaSH solution consisting of 44.96 percent NaSH and 0.62 percent $Na_2S$, 77.61 g of aqueous NaOH solution containing 50.4 percent NaOH, and 86.61 g of flake sulfur. The mixture was vigorously stirred at 70 degrees Celsius (Centigrade) until all of the solids were dissolved. Then 14.54 g of a 25 percent aqueous tetrabutylammonium bromide (TBAB) solution were added. After adding TBAB, 460 g of chloropropyltriethoxysilane (CPTES) were added over 77 minutes, and the temperature was maintained at between 72–78 degrees Celsius. After all of the chloropropyltriethoxysilane had been added, the mixture continued to be agitated, and the temperature was controlled in the range of 73–75 degrees Celsius, for another 47 minutes until gas chromatograph results showed that the chloropropyltriethoxysilane concentration in the product had leveled. The mixture was then heated to 84–85 degrees Celsius, and maintained at that temperature with continued agitation for 83 minutes. The mixture was then cooled to 55 degrees Celsius, and 131.63 g of water was added. The mixture was stirred until all of the formed salts were dissolved. The mixture was phase separated at 47 degrees Celsius, and 434.3 g of a yellow aqueous phase were drained from the bottom of the reactor. The remaining organic phase was cooled to 19 degrees Celsius, and then filtered to produce 474.85 g of a clear, light green-yellow product. High pressure liquid chromatography (HPLC) analysis showed an average sulfur rank of 3.52, and quantitative gas chromatography analysis showed 0.44 percent of unreacted chloropropyltriethoxysilane.

Example 2

A 1.5 L jacketed glass reactor equipped with a motor-driven impeller, a single baffle, thermocouple, and addition funnel, was loaded at ambient temperature with 46.42 g of water, 113.21 g aqueous NaSH solution consisting of 45.82 percent NaSH and 0.01 percent $Na_2S$, 74.09 g of aqueous NaOH solution containing 50.4 percent NaOH, and 86.01 g of flake sulfur. The mixture was vigorously stirred at 70 degrees Celsius until all solids had been dissolved. Then 15.27 g of a 25 percent aqueous tetrabutylammonium bromide solution were added. After addition of TBAB, 459 g of chloropropyltriethoxysilane were added over 45 minutes, and the temperature was maintained at between 72–77 degrees Celsius. When all of the chloropropyltriethoxysilane had been added, agitation of the mixture continued, and the temperature was controlled in the range of 75–77 degrees Celsius for another 65 minutes, until gas chromatograph results showed that the chloropropyltriethoxysilane concentration in the product had leveled. The mixture was then heated to 88–89 degrees Celsius and maintained at that temperature with continued agitation for 72 minutes. Then the mixture was cooled to 62 degrees Celsius, and 140.42 g of water were added. The mixture was stirred until all of the formed salts had been dissolved. The mixture was phase separated at 47 degrees Celsius, and 422.05 g of a clear and colorless aqueous phase was drained from the bottom of the reactor. The organic phase was then transferred to a stripping apparatus, where it was stripped to remove residual water, and agitated via a stir bar at 30 mm Hg and 100–101 degrees Celsius for 166 minutes. The organic phase was then filtered to produce 434.12 g of a clear, light yellow product. HPLC analysis showed an average sulfur rank of 3.61 and quantitative gas chromatography analysis showed 0.36 percent of unreacted chloropropyltriethoxysilane.

Example 3

A 1.5 L jacketed glass reactor equipped with a motor-driven impeller, a single baffle, thermocouple, and an addition funnel, was loaded at ambient temperature with 124.64 g of water, 228.94 g aqueous NaSH solution consisting of 45.62 percent NaSH and 0.01 percent $Na_2S$, 148.24 g of an aqueous NaOH solution containing 50.4 percent NaOH, and 173.62 g of flake sulfur. The mixture was vigorously stirred at 73 degrees Celsius until all of the solids had been dissolved. Then 14.6 g of a 50 percent aqueous tetrabutylammonium bromide solution were added. After adding TBAB, 919.3 g of chloropropyltriethoxysilane were added over 112 minutes, and the temperature was maintained at between 70–83 degrees Celsius. When all of the chloropropyltriethoxysilane had been added, agitation of the mixture continued, and the temperature was controlled in the range of 73–77 degrees Celsius for another 117 minutes, until gas chromatograph results showed that the chloropropyltriethoxysilane concentration in the product had leveled. The mixture was then heated to 90–91 degrees Celsius and held at that temperature while agitation continued for 114 minutes. The organic phase was transferred to a stripping apparatus where it was stripped and agitated via a stir bar at 50 mm Hg and 95–99 degrees Celsius for 112 minutes. The organic phase was filtered to produce 855.1 g of a clear, light yellow-orange product. HPLC analysis showed an average sulfur rank of 3.74 and quantitative gas chromatography analysis showed 0.35 percent of unreacted chloropropyltriethoxysilane. The aqueous phase remaining in the reactor was cooled to 66 degrees Celsius, and 261.02 g of water were added. The mixture was stirred until all of the formed salts had been dissolved, and 888.7 g of a clear and colorless aqueous phase were drained from the reactor.

Example 4

A manufacturing scale jacketed glass-lined batch reactor equipped with a motor-driven impeller, a single baffle, and a thermocouple, was loaded starting at ambient temperature with 6.1 parts of water, 12.0 parts of an aqueous NaSH solution consisting of 46.05 percent NaSH and 0.55 percent $Na_2S$, 8.5 parts of aqueous NaOH solution containing 46.3 percent NaOH, and 9.3 parts of flake sulfur. The mixture was vigorously stirred at 75 degrees Celsius until all of the solids had been dissolved. Then 0.8 parts of a 50 percent aqueous tetrabutylammonium bromide solution were added. After the TBAB had been added, 49.3 parts of chloropropyltriethoxysilane were added over 3 hours, and the temperature was maintained between 69–82 degrees Celsius. When all of the chloropropyltriethoxysilane had been added, agitation of the mixture continued, and the temperature was controlled in the range of 71–77 degrees Celsius for another 4⅓ hours, until the gas chromatograph results showed that the chloropropyltriethoxysilane concentration in the product had leveled. The mixture was then heated to 87–91 degrees Celsius, and held at that temperature while agitation continued for 2 hours. The mixture was cooled to 50 degrees Celsius, and 14.0 parts of water were added. The mixture was stirred until all of the formed salts had been dissolved. The mixture was phase separated at 44 degrees Celsius, and 46.6 parts of a clear and colorless aqueous phase were drained from the bottom of the reactor. The organic phase was stripped to remove residual water at 50 mm Hg and 95–104 deg C. for 4⅓ hours. The remaining organic phase was cooled to 19 degrees Celsius, and then filtered, producing 53.4 parts of a clear light yellow-orange product. HPLC analysis showed an average sulfur rank of 3.77 and quantitative gas chromatography analysis showed 2.11 percent of unreacted chloropropyltriethoxysilane.

Example 5

A manufacturing scale jacketed glass-lined batch reactor equipped with a motor-driven impeller, a single baffle, and a thermocouple, was loaded at ambient temperature with 6.3 parts of water, 12.0 parts of an aqueous NaSH solution consisting of 46.07 percent NaSH and 0.55 percent $Na_2S$, 8.3 parts of aqueous NaOH solution containing 47.52 percent NaOH, and 9.3 parts of flake sulfur. The mixture was vigorously stirred at 65–75 degrees Celsius until all of the solids had been dissolved. Then 0.8 parts of a 50 percent aqueous tetrabutylammonium bromide solution were added. After adding TBAB, 49.3 parts of chloropropyltriethoxysilane were added over 3.5 hours, and the temperature was maintained between 67–78 degrees Celsius. When all of the chloropropyltriethoxysilane had been added, agitation of the mixture continued, and the temperature was controlled in the range of 71–77 degrees Celsius for another 6 hours, until gas chromatograph results showed that the chloropropyltriethoxysilane concentration in the product had leveled. The mixture was then heated to 87–92 degrees Celsius and maintained at that temperature as agitation continued for 2 hours. The mixture was cooled to 53 degrees Celsius, and 14.0 parts of water were added to the reactor. The mixture was stirred until all of the formed salts had been dissolved. The mixture was phase separated at 45 degrees Celsius, and 46.5 parts of a clear and colorless aqueous phase were drained from the bottom of the reactor. The organic phase was then stripped to remove residual water at 100–120 mm Hg and 95–100 deg C. for 4 hours. The remaining organic phase was cooled to 19.5 degrees Celsius, and filtered to produce 53.5 parts of a clear light yellow-orange product. HPLC analysis showed an average sulfur rank of 3.75 and quantitative gas chromatography analysis showed 1.96 percent of unreacted chloropropyltriethoxysilane.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A process for producing sulfur containing organosilicon compounds having the formula $(RO)_{3-m}R_mSi$—Alk—$S_n$—Alk—$SiR_m(OR)_{3-m}$ wherein R represents independently a monovalent hydrocarbon having 1–12 carbon atoms, Alk represents a divalent hydrocarbon having 1–18 carbon atoms, m is an integer representing 0, 1 or 2, n is an integer with a value of 2–8, comprising the steps of (I) heating and reacting (A) a sulfide compound having the formula $M_2S_n$ or MHS wherein H is hydrogen, M is ammonium or an alkali metal, and n is 1–8, with (B) a silane compound having the formula $(RO)_{3-m}R_mSi$—Alk—X wherein X is Cl, Br or I, and m is 0, 1, or 2, and (C) sulfur, in the presence of a phase transfer catalyst and an aqueous phase containing a buffer or a basic compound, to form a product mixture, (II) heating the product mixture to a temperature of 80–100° C., and (III) separating the organosilicon compound from the product mixture.

2. The process of claim 1 wherein the organosilicon compound is separated from the product mixture by (D) adding water or a dilute acidic solution to the product mixture, and (E) phase separating the product mixture into an organic phase containing the organosilicon compound and an aqueous phase.

3. The process of claim 2 wherein the weight percent of water or dilute acidic solution to silane compound (B) is 10–50 percent.

4. The process of claim 2 wherein the organic phase containing the organosilicon compound is dried by heating the organic phase at a reduced pressure.

5. The process of claim 2 wherein the organic phase containing the organosilicon compound is dried by contacting the organic phase with a solid desiccant selected from the group consisting sodium sulfate, magnesium sulfate, calcium sulfate, calcium chloride, magnesium chloride, lithium chloride, molecular sieves, zeolites, aluminasilicates, and silica gel.

6. The process of claim 2 comprising the additional steps of (F) cooling the organic phase containing the organosilicon compound to a temperature below 15° C. to precipitate unreacted sulfur compounds, and (G) separating the organic phase containing the organosilicon compound from the precipitated unreacted sulfur compounds.

7. The process of claim 6 wherein cooling step (F) is at temperatures in the range of −20 to 10° C.

8. The process of claim 1 wherein the heating in step (II) is at a temperature of 85–95° C.

* * * * *